(12) United States Patent
Jang

(10) Patent No.: US 12,287,635 B2
(45) Date of Patent: Apr. 29, 2025

(54) ROBOT TO CARRY USED TREATMENT TOOL TO DISINFECTION ROOM

(71) Applicant: Kwan Ik Jang, Hanam-si (KR)

(72) Inventor: Kwan Ik Jang, Hanam-si (KR)

(*) Notice: Subject to any disclaimer, the term of this patent is extended or adjusted under 35 U.S.C. 154(b) by 206 days.

(21) Appl. No.: 18/201,009

(22) Filed: May 23, 2023

(65) Prior Publication Data
US 2024/0061432 A1  Feb. 22, 2024

(30) Foreign Application Priority Data
Aug. 18, 2022 (KR) .......... 10-2022-0103014

(51) Int. Cl.
*G05D 1/00* (2006.01)
*A61L 2/24* (2006.01)

(52) U.S. Cl.
CPC .............. *G05D 1/0214* (2013.01); *A61L 2/24* (2013.01); *G05D 1/0276* (2013.01); *A61L 2202/24* (2013.01)

(58) Field of Classification Search
CPC .............. G05D 1/0214; G05D 1/0276; G05D 2105/28; G05D 2107/65; G05D 1/646; G05D 1/244; G05D 2109/10; A61L 2/24; A61L 2202/24; A61L 2202/16
USPC ......................................................... 701/23
See application file for complete search history.

(56) References Cited

U.S. PATENT DOCUMENTS

2022/0088241 A1* 3/2022 Braverman ............... A61L 9/20

FOREIGN PATENT DOCUMENTS

| DE | 112020000477 | * | 10/2021 |
|----|--------------|---|---------|
| EP | 3914301 | * | 12/2021 |
| KR | 10-1280908 B1 | | 7/2013 |
| KR | 20190055415 | * | 5/2019 |
| KR | 20210156786 | * | 12/2021 |
| WO | WO-2020151918 | * | 7/2020 |

* cited by examiner

*Primary Examiner* — Muhammad Shafi
(74) *Attorney, Agent, or Firm* — Bridgeway IP Law Group, PLLC; Sang Ho Lee; Hyun Woo Shin

(57) ABSTRACT

Provided is a robot for transporting patient treatment tools. The robot includes a main body providing a space open in a front side of the main body and capable of traveling on the ground; a communication unit installed in the main body and wirelessly connected to the call signal generator; a control unit located on an upper side of the main body and manipulated by a user; an elevating structure slidably installed in the space of the main body; elevating means for elevating the elevating structure; a storage box supported by the elevating structure, temporarily accommodating treatment tools introduced from the outside, being movable forwards and backwards, and moving forwards and opened to send the treatment tools to the outside; and a storage box driving unit for moving the storage box forwards and backwards.

3 Claims, 8 Drawing Sheets

ROBOT TO CARRY USED TREATMENT TOOL TO DISINFECTION ROOM

CROSS-REFERENCE TO RELATED APPLICATION

This application claims priority to Korean patent application No. 10-2022-0103014, filed on Aug. 18, 2022, the entire disclosure of which is incorporated herein by reference.

TECHNICAL FIELD

The present invention relates to a transport robot for transporting treatment tools used in hospitals, and more particularly, to a robot for transporting treatment tools for patients, which performs an operation of transporting used treatment tools from a treatment room to a disinfection room.

BACKGROUND ART

Various treatment tools used in dentistry, such as handpieces, mirrors, tweezers, explorers, and scalers, must be cleaned and sterilized after use. In particular, fine bone powder or contaminants may deeply penetrate through and be fixed to tools used in, for example, tooth removal or polishing, and thus thorough hygiene management is essential.

The disinfection effect for treatment tools improves as a disinfection time is extended. Accordingly, it is preferable to operate a plurality of frequently used treatment tools so that a used treatment tool may be disinfected as long as possible.

In dental hospitals, there is a separate disinfection room for sterilizing used treatment tools. Nurses or officials collect used treatment tools discharged from the treatment room, transport them to the disinfection room, and then proceed with appropriate disinfection.

However, in the case of large-sized general hospitals, a distance between a treatment room and a disinfection room is not close to each other, and accordingly, it is very inconvenient for nurses to visit the disinfection room with treatment tools every time. In addition, even when professional personnel to collect treatment tools are operated, the time when a treatment tool is discharged for each treatment room is not determined, and thus it is very cumbersome and inefficient for the professional personnel to be contacted and visit the treatment room to collect treatment tools whenever the treatment tools are discharged.

There is a demand for automatic transportation means that visits a treatment room on behalf of a person, collects treatment tools, and transports them to a disinfection room when there is a signal to discharge a treatment tool from the treatment room.

Korean Patent Registration No. 10-1280908 (device and method of driving an object transfer tug robot with excellent self-location tracking and obstacle avoidance) has been proposed as means used for transporting an object in a hospital or the like.

DESCRIPTION OF EMBODIMENTS

Technical Problem

Provided is patient treatment tools transportation robot capable of replacing the previous hassle of people by performing, under its own judgment, a series of actions of visiting a treatment room that has generated a call signal, receiving a treatment tool discharged from the treatment room, and transporting the received treatment tool to a disinfection room.

Technical Solution

According to an embodiment of the present invention, a robot for transporting patient treatment tools reciprocates between a treatment room having a call signal generator installed therein and a disinfection room, visits, in response to a call signal, the treatment room where the call signal has been generated, receives a treatment tool discharged from the treatment room, and transports the received treatment tool to the disinfection room. The robot includes a main body providing a space open in a front side of the main body and capable of traveling on the ground; a communication unit installed in the main body and wirelessly connected to the call signal generator; a control unit located on an upper side of the main body and manipulated by a user; an elevating structure slidably installed in the space of the main body; elevating means for elevating the elevating structure; a storage box supported by the elevating structure, temporarily accommodating treatment tools introduced from the outside, being movable forwards and backwards, and moving forwards and opened to send the treatment tools to the outside; and a storage box driving unit for moving the storage box forwards and backwards.

In the disinfection room, a sink having a disinfection tank is installed, and a to-be-sensed member that informs the robot of the height of the disinfection tank is provided on a front surface of an upper end of the sink. The elevating structure includes a support plate that maintains a level; load bearings fixed onto an upper surface of the support plate in parallel to each other, extending forwards and backwards, and movably supporting the storage box; and side plates fixed vertically on both sides of the supporting plate. A height sensor for sensing the to-be-sensed member and generating a signal when the support plate is located at the same height as the to-be-sensed member is installed in the elevating structure, and the storage box driving unit is a linear motor that provides a transfer force to the storage box while being mounted on the elevating structure.

The storage box includes a casing having an inlet in an upper portion of the storage box and an outlet in a front portion of the storage box and reciprocating by a linear motor while being supported by the load bearings; and an outlet opening/closing unit accommodated in the casing and serving to receive and support treatment tools introduced from the outside through the inlet and to open or block the outlet by moving due to an external force.

The outlet is located eccentrically on a lower portion of a front surface of the casing, and the outlet opening/closing unit includes a slide being a rectangular plate member, being supported through a support pin within the casing, being rotatable about the support pin, maintaining a height higher than the outlet in a horizontal state, and blocking the outlet while supporting the treatment tool to be discharged; and an opening/closing actuator linked to the slide, and keeping the slide horizontal or being inclined toward the outlet so that the treatment tool slides on the slide to pass through the outlet.

Effects of Disclosure

A patient treatment tool transportation robot according to the present invention having such a structure as described above may replace the previous hassle of people by performing, under its own judgment, a series of actions of visiting a treatment room that has generated a call signal, receiving a treatment tool discharged from the treatment room, and transporting the received treatment tool to a disinfection room.

DETAILED DESCRIPTION

An embodiment of the present invention will now be described in more detail with reference to the accompanying drawings.

Figure 1:
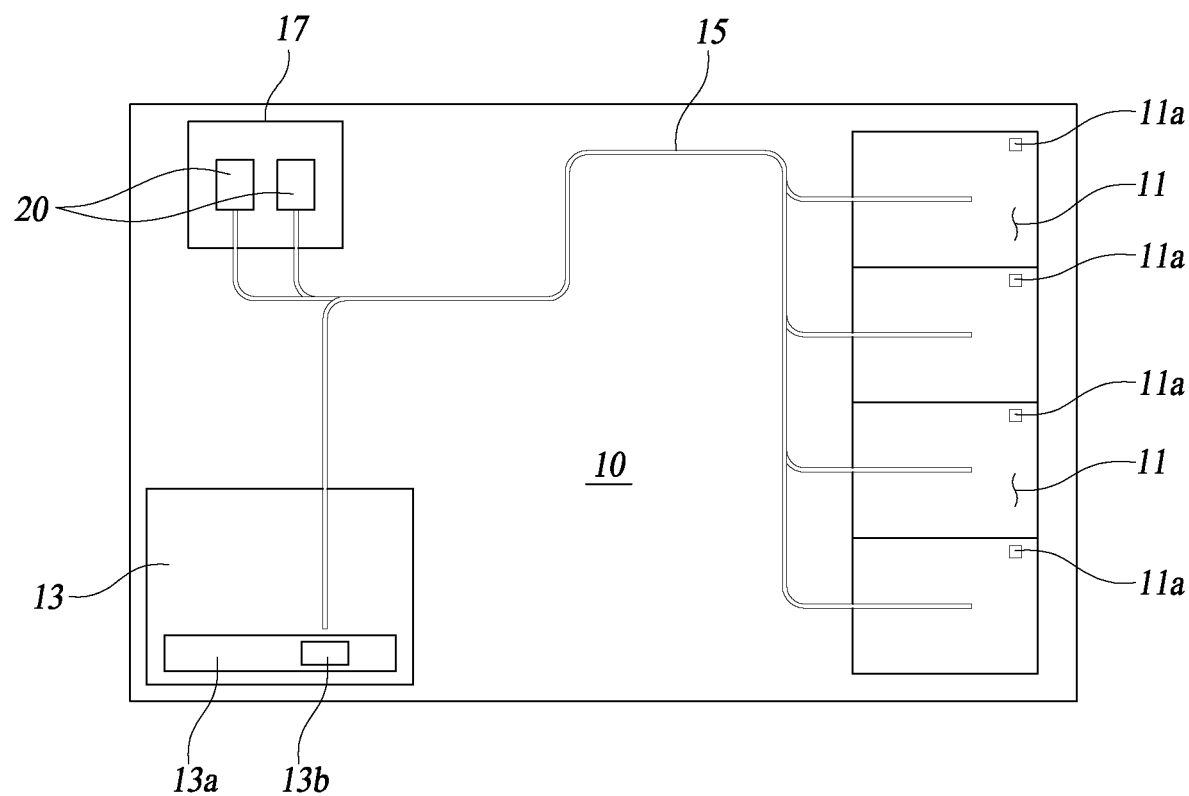
FIG. 1 is a plan view of an indoor space for explaining a method of using a robot for transporting patient treatment tools, according to an embodiment of the present invention.

FIG. 1 is a plan view of an indoor space 10 for explaining a method of using a robot 20 for transporting patient treatment tools, according to an embodiment of the present invention.

As shown in FIG. 1, a plurality of treatment rooms 11 and a disinfection room 13 are arranged in the interior of a hospital, and a wireless charging room 17 is located at one corner. Treatments are performed in the treatment rooms 11.

A call signal generator 11a is installed in each of the treatment rooms 11. The call signal generator 11a is a switch operated by a doctor or nurse. When the call signal generator 11a is pressed, the robot 20 visits the treatment room 11. The robot 20 and the call signal generator 11a are connected to each other by short-distance wireless communication. The robot 20 receives a used treatment tool discharged from the treatment room 11 and transports the used treatment tool to the disinfection room 13.

In the disinfection room 13, related equipment (not shown) for sterilizing and disinfecting treatment tools and a sink 13a are located. A disinfection tank 13b is installed in the sink 13a. A disinfectant solution is contained in the disinfectant tank 13b. A to-be-sensed member 13c is disposed on a front surface of the sink 13a. The to-be-sensed member 13c is sensed by a height sensor 37 to be described later, and informs the height of the disinfection tank 13b.

When the robot 20 receives a call signal while waiting in the wireless charging room 17, the robot 20 repeats actions of visiting the treatment room 11, receiving a used treatment tool, moving to the disinfection room 13, and putting the used treatment tool into the disinfection tank 13b. The robot 20 replaces a cumbersome work that previously depends on manpower.

A travel detection line 15 is disposed on the floor of the indoor space 10. The travel detection line 15 is a movement line for the robot 20. The robot 20 travels along the travel detection line 15. This traveling method is general, and thus a description thereof will be omitted.

Figure 2:
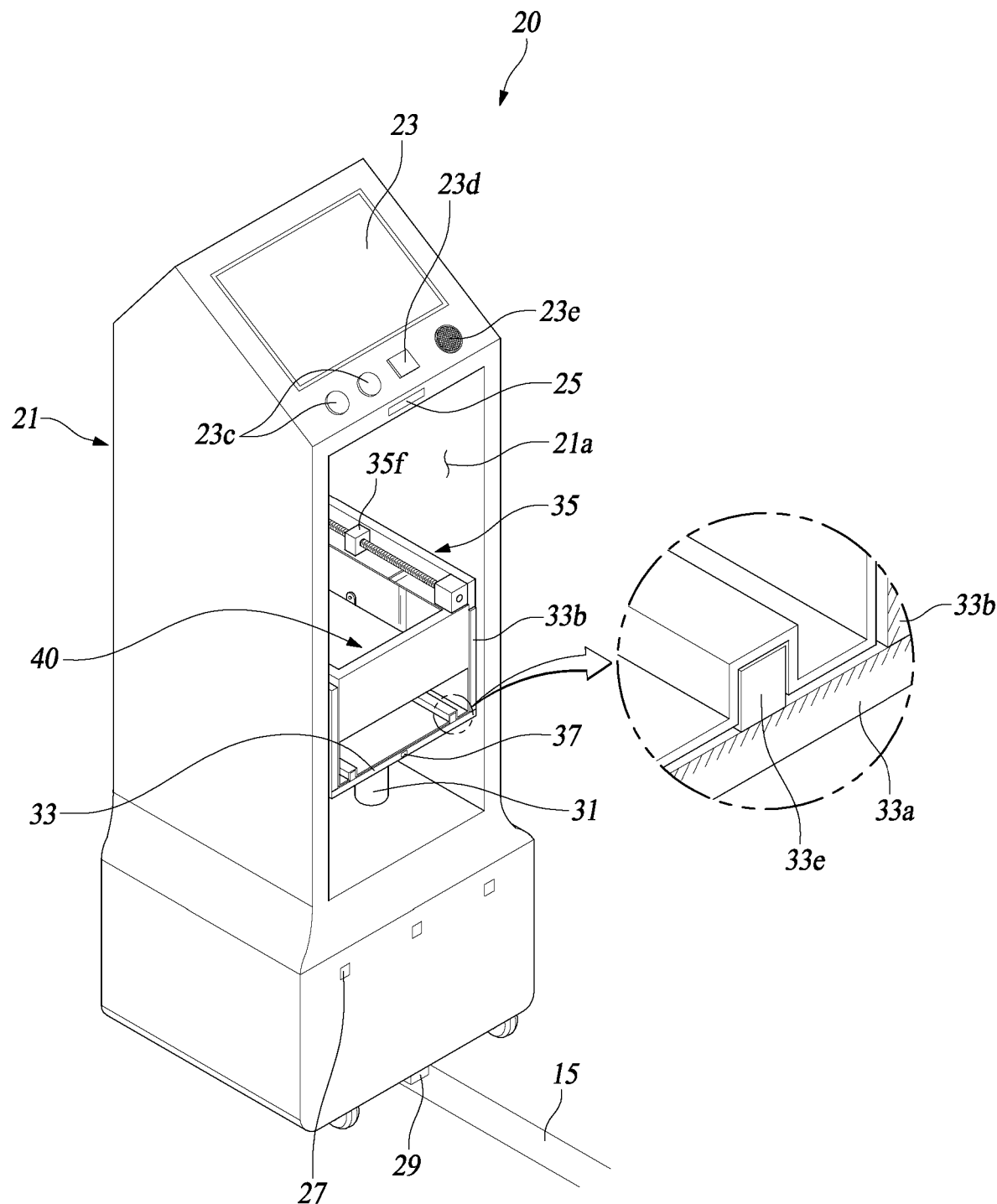
FIG. 2 is a perspective view of a robot for transporting patient treatment tools, according to an embodiment of the present invention.
Figure 3:
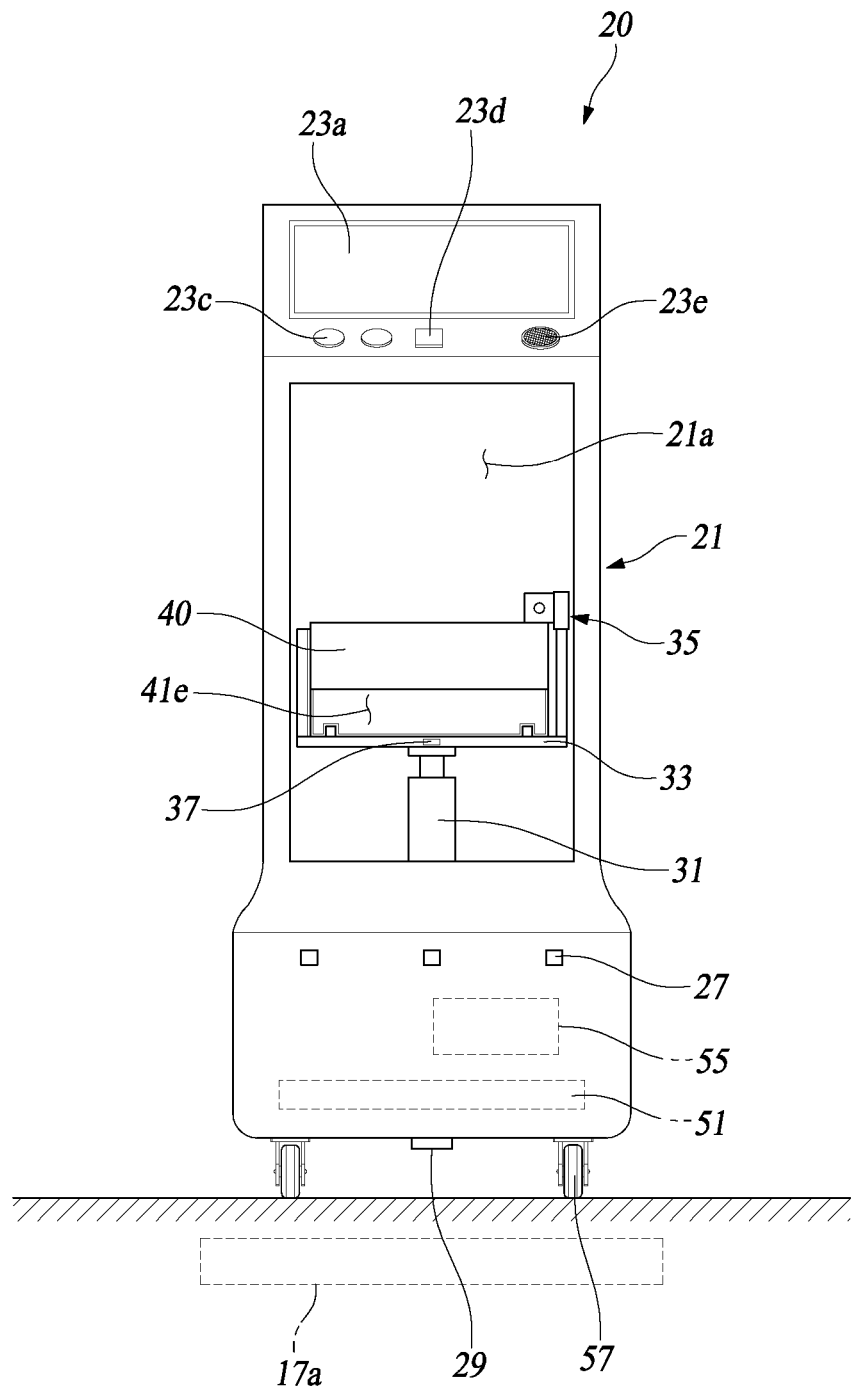
FIG. 3 is a front view of the robot of FIG. 2.
Figure 4:
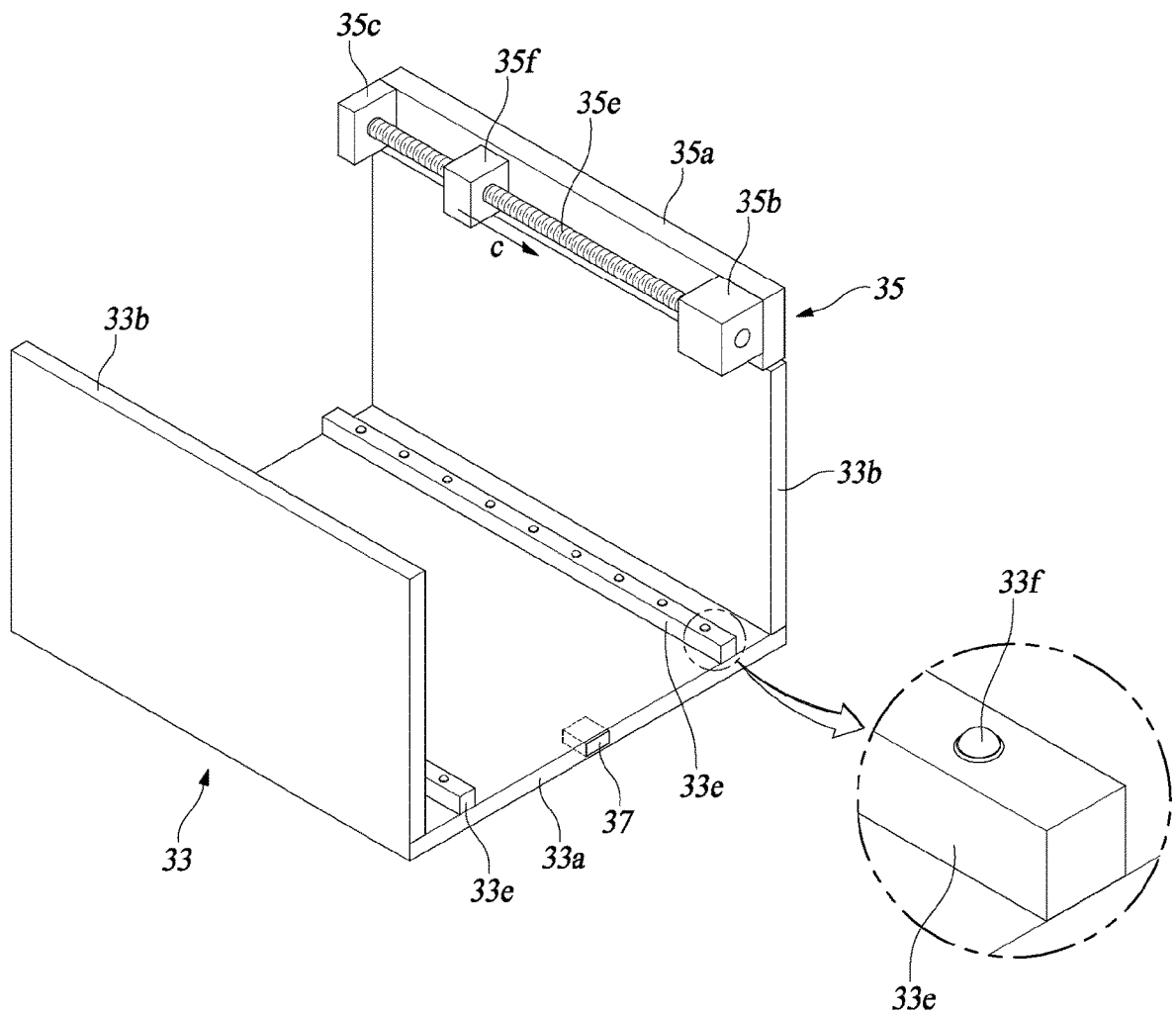
FIG. 4 is a perspective view separately showing an elevating structure and a linear motor of FIG. 3.
Figure 5:
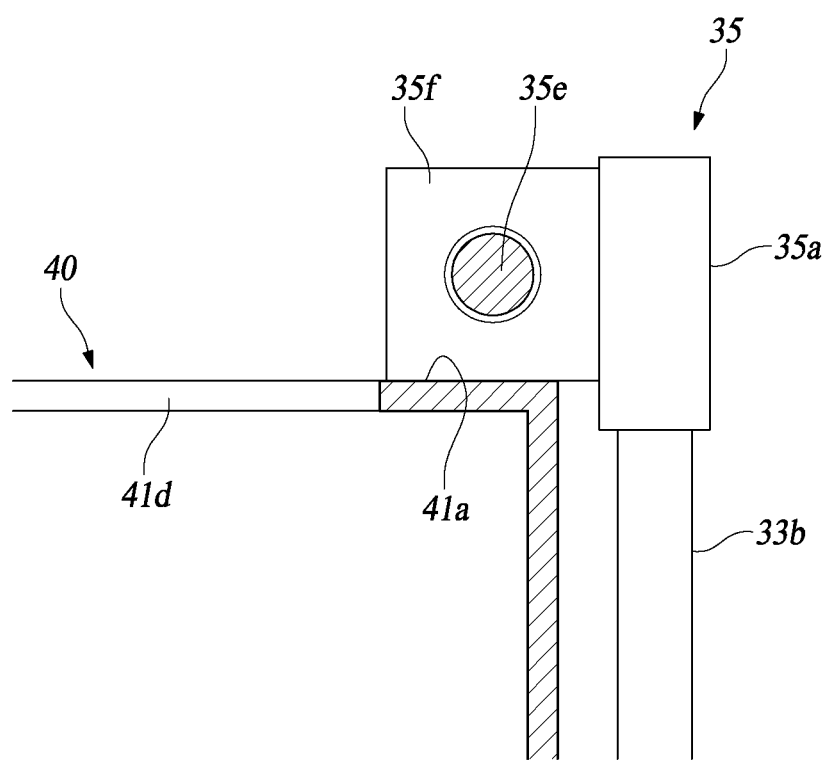
FIG. 5 is a view for explaining a connection structure between the linear motor of FIG. 4 and a storage box.
Figure 6:
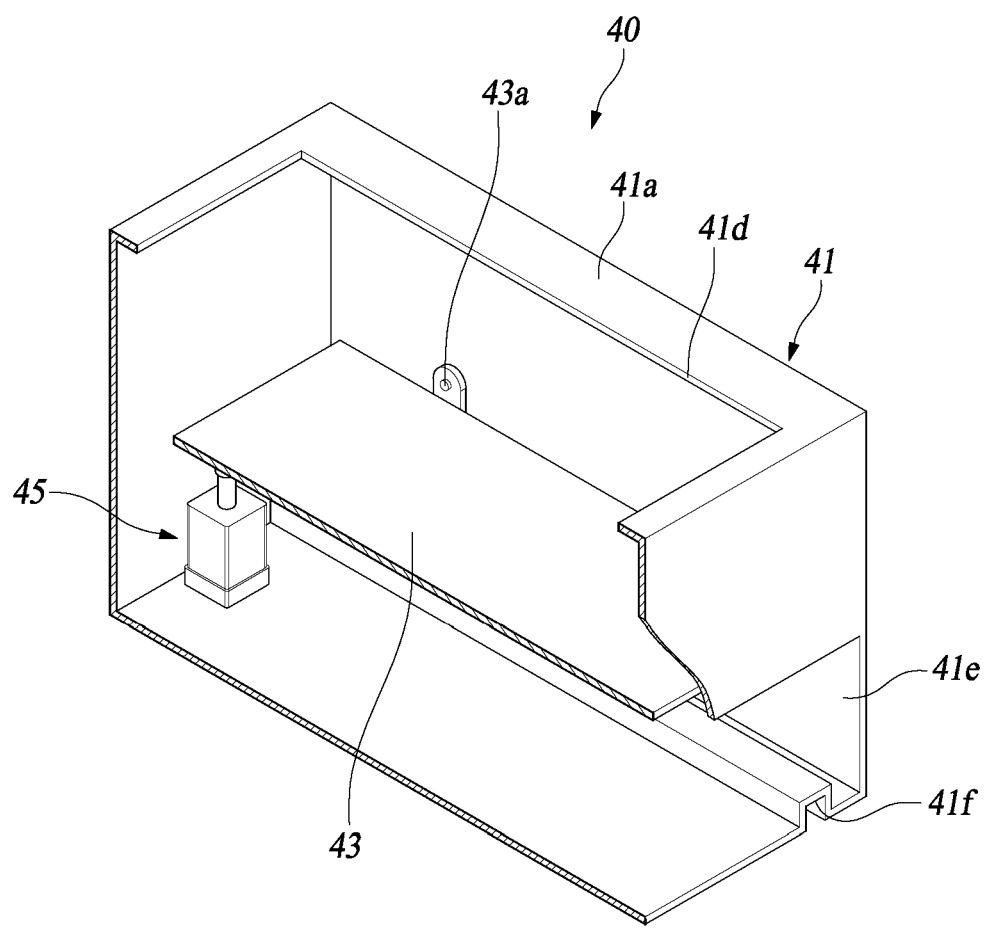
FIG. 6 is a cutaway perspective view of the storage box shown in FIG. 2.
Figure 7A:
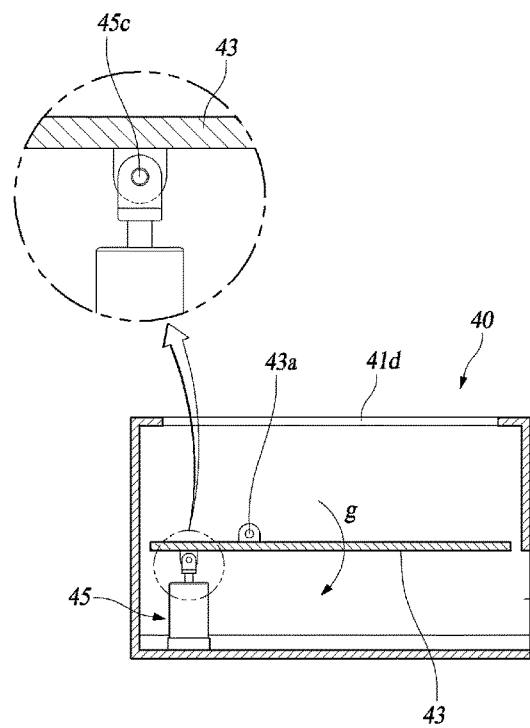
FIGS. 7A and 7B are views for explaining an operation of the storage box of FIG. 6.
Figure 7B:
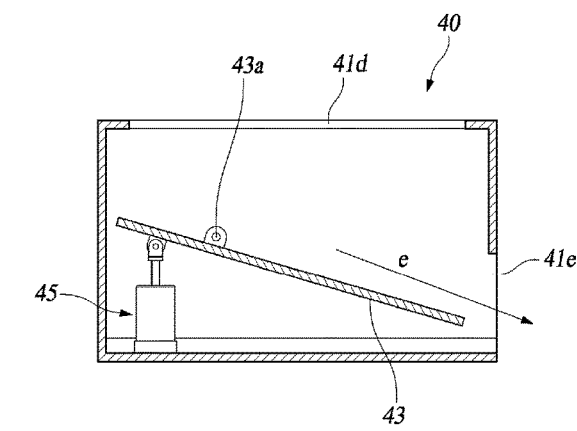

FIG. 2 is a perspective view of the robot 20 for transporting patient treatment tools, according to an embodiment of the present invention. FIG. 3 is a front view of the robot 20 of FIG. 2. FIG. 4 is a perspective view separately showing an elevating structure and a linear motor of FIG. 3, and FIG. 5 is a view for explaining a connection structure between the linear motor of FIG. 4 and a storage box. FIG. 6 is a cutaway perspective view of the storage box shown in FIG. 2, and FIGS. 7A and 7B are views for explaining an operation of the storage box of FIG. 6.

As described above, the robot 20 according to the present embodiment is a machine that reciprocates between each treatment room 11 in which the call signal generator 11a is installed and the disinfection room 13. In other words, in response to a call signal, the robot 20 visits a treatment room 11 where the call signal is generated, receives a treatment tool discharged from the treatment room 11, and transports the received treatment tool to the disinfection room 13. The reason why the treatment tool is transported to the disinfection room 13 is definitely to be sterilized.

As shown in FIG. 2, the robot 20 according to the present embodiment includes a main body 21, a communication unit 25, a control unit 23, an elevating structure 33, elevating means, a storage box 40, and a storage box driving unit.

The main body 21 travels along the travel detection line 15 in a state of standing on the ground, and provides a space 21a on a front side in a travel direction. As shown in FIG. 3, a wireless power reception unit 51 and a battery 55 are built in a lower portion of the inside of the main body 21.

In a state of being located over a wireless power transmission unit 17a, the wireless power reception unit 51 receives a magnetic force from the wireless power transmission unit 17a and then converts the magnetic force into electricity. The converted electricity is charged in the battery 55. This wireless charging method is general, and thus a description thereof will be omitted. The wireless power transmission unit 17a is located below the ground (floor surface) of the wireless charging room 17.

The battery 55, which is a rechargeable battery, supplies power necessary for driving the robot 20. Of course, the battery 55 may be charged in a wired manner.

A plurality of wheels 57 are installed on the bottom of the main body 21. The wheels 57 receive a control signal output through the control unit 23 and perform a rolling motion so that the robot 20 travels along a path.

A tracking sensor 29 is installed on the bottom surface of the main body 21. The tracking sensor 29 senses the travel detection line 15. While the robot 20 is moving, the tracking sensor 29 continuously senses the travel detection line 15 and sends detection information to the control unit 23. The control unit 23 controls the traveling of the robot 20 through the detection information of the tracking sensor 29.

Obstacle sensors 27 are installed on front and rear surfaces of the main body 21. The obstacle sensors 27 sense obstacles while the robot 20 is traveling. Sensing information of the obstacle sensors 27 is transmitted to the control unit 23 in real time. When the robot 20 encounters an obstacle while traveling, the robot 20 immediately stops.

The communication unit 25, which is a communication module located above the space unit 21a, is wirelessly connected to the call signal generators 11a. Signals output by the call signal generators 11a are transmitted to the communication unit 25. The signal reception by the communication unit 25 is transmitted to the control unit 23 so that the control unit 23 performs appropriate control.

The control unit 23 is positioned in an upper portion of the main body 21 and controls the overall operation of the robot 20. For example, the control unit 23 controls forward/backward travel of the robot 20, route selection at a forked road, operations of the elevating means, the storage box driving unit, and the storage box 40, and driving of the communication unit 25. The control unit 23 is implemented in a touch panel manner. A user may input data or commands by touching the control unit 23, and may check various types of information provided by the robot through a screen 23a of the control unit 23.

Buttons 23c, a lamp 23d, and a speaker 23e are positioned below the control unit 23. The buttons 23c are switches for forcibly stopping the robot 20 in an emergency or manually operating the lamp 23d. The lamp 23d is turned on when the robot 20 moves, and informs neighboring people that the robot 20 is moving. The speaker 23e outputs various types of sound information.

The elevating means is an elevating actuator 31 installed vertically on the bottom of the space unit 21a. The elevating actuator 31, which is an electromagnetic actuator, elevates the elevating structure 33. In other words, the elevating actuator 31 lowers the elevating structure 33 as much as possible in a standby state, and, before moving the storage box 40 forwards as shown in FIG. 8B, the elevating actuator 31 raises the elevating structure 33. The elevating structure 33 stops when the height sensor 37 is positioned at the same height as the to-be-sensed member 13c.

The elevating structure 33 is elevated by the elevating actuator 31 and has the structure shown in FIG. 4. As shown in FIG. 4, the elevating structure 33 has a support plate 33a, load bearings 33e, and side plates 33b.

The support plate 33a, which is a rectangular plate having a certain thickness, is fixed to an upper end of the elevating actuator 31, and supports the storage box 40 and a linear motor 35.

The load bearings 33e are linear members fixed onto an upper surface of the support plate 33a in parallel with each other, and have a plurality of support balls 33f. The support balls 33f, which are bearing balls, may roll. The load bearings 33e guide a linear motion of a casing 41 while being accommodated in bearing mounting grooves 41f formed on the bottom of a casing 41.

The side plates 33b are plate members vertically fixed to upper surfaces of both ends of the support plate 33a in a width direction, and the storage box drive unit is mounted on one of the two side plates 33b.

The storage box driving unit is the linear motor 35 that serves to linearly move the storage box 40 accommodated in the elevating structure 33 forwards and backwards. The linear motor 35 includes a fixing body 35a, an actuation motor 35b, a lead screw 35e, a support block 35c, and a connecting block 35f.

The fixing body 35a is vertically fixed to a top surface of a side plate 33b and provides a supporting force. The actuation motor 35b is installed on one end of the fixing body 35a, and the support block 35c is installed on the other end thereof. The lead screw 35e is fixed to a driving shaft of the actuation motor 35b. An end of the lead screw 35e is supported by the support block 35c so as to be axially rotated.

The connecting block 35f meshes with the lead screw 35e. The connecting block 35f is fixed to a connector fixing unit 41a (see FIG. 5) of the storage box 40. When the lead screw 35e axially rotates, the connecting block 35f linearly moves in a direction indicated by an arrow c or in its opposite direction. At this time, the storage box 40 naturally moves together with the connecting block 35f.

The storage box 40 serves to temporarily accommodate treatment tools introduced from the outside and to pour out the accommodated treatment tools into the disinfection tank 13b when being located above the disinfection tank 13b. The storage box 40 may slide in forward and backward directions by means of the linear motor 35.

The storage box 40 is composed of the casing 41 and an outlet opening/closing unit. The outlet opening/closing unit includes a slide 43 and an opening/closing actuator 45.

The casing 41, which is a hexahedral box, has an inlet 41d in its top portion and an outlet 41e in its front portion. The inlet 41d is a passage for receiving treatment tools. In other words, a doctor or nurse inserts treatment tools used once into the inlet 41d. The connector fixing unit 41a is provided on one side of the inlet 41d. The connector fixing unit 41a is a portion to which the connecting block 35f is fixed.

The outlet 41e is a passage through which a treatment tool moving in a direction indicated by an arrow e of FIG. 7B passes. The outlet 41e is located eccentrically on a lower portion of the front surface of the casing 41. The bearing mounting grooves 41f are formed on the bottom surface of the casing 41. The bearing mounting grooves 41f are slit-type grooves into which the load bearing 33e described above are inserted.

The outlet opening/closing unit is accommodated in the casing 41 and serves to receive and support treatment tools introduced from the outside through the inlet 41d and to open or block the outlet 41e by moving due to an external force.

The slide 43 included in the outlet opening/closing unit is a rectangular plate having a certain thickness, and is rotatably supported through a support pin 43a. In other words, the slide 43 may rotate in a direction indicated by an arrow g or in its opposite direction by using the support pin 43a as a central axis of rotation. The slide 43 is kept level in normal times. In particular, a height of the slide 43 in a state of being kept horizontal is higher than that of the outlet 41e. Therefore, treatment tools temporarily accommodated above the slide 43 may not escape through the outlet 41e.

In order to discharge a treatment tool supported by the slide 43 through the outlet 41e, the slide 43 needs to be tilted by being rotated in the direction indicated by the arrow g. When the slide 43 is tilted, the treatment tool slides on the slide 43 and is discharged to the outside.

The opening/closing actuator 45 serves to rotate the slide 43. The opening/closing actuator 45 is an electronic actuator. As shown in FIG. 7A, the opening/closing actuator 45 is linked to the slide 43 through a connecting pin 45c while being located below the slide 43. By the opening/closing actuator 45, the slide 43 is maintained level, or is inclined downwards toward the exit 41e as shown in FIG. 7B.

Figure 8A:
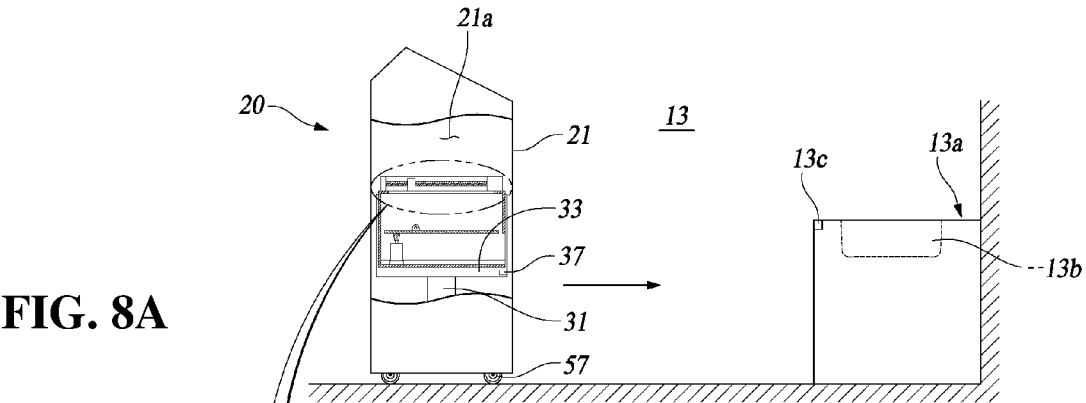
FIGS. 8A, 8B, and 8C are views for explaining an operating method of a robot for transporting patient treatment tools, according to an embodiment of the present invention.
Figure 8B:
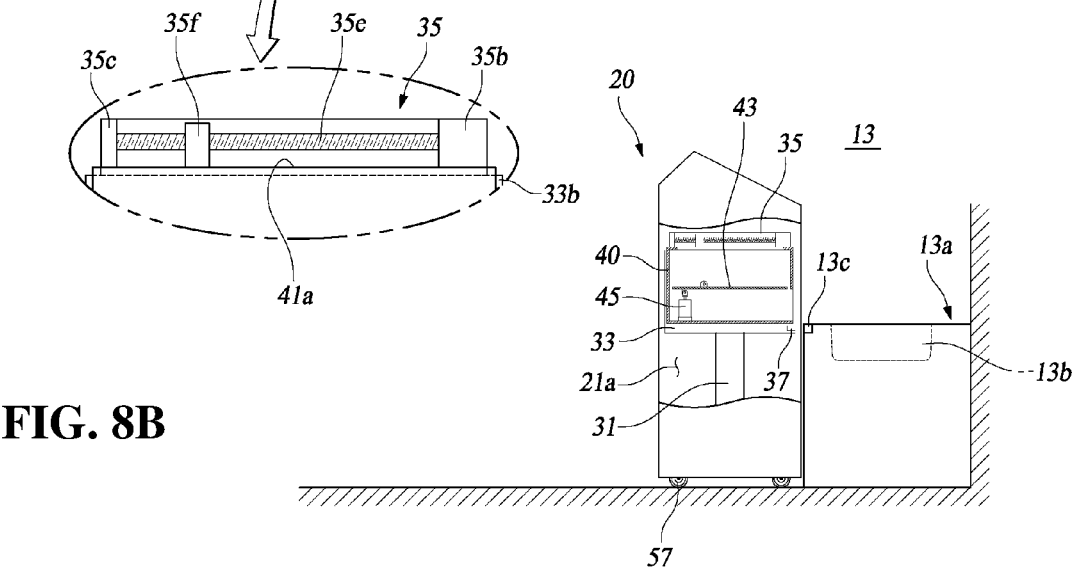
Figure 8C:
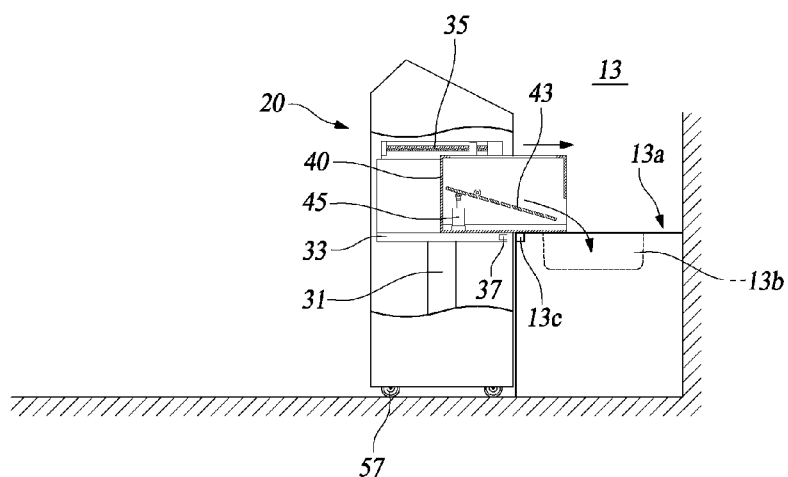

FIGS. 8A, 8B, and 8C are views for explaining an operating method of a robot for transporting patient treatment tools, according to an embodiment of the present invention.

As shown in FIG. 8A, the sink 13a having the disinfection tank 13b is installed in the disinfection chamber 13. The to-be-sensed member 13c informing the robot 20 of the height of the disinfection tank 13b is fixed to the front surface of an upper end of the sink 13a.

First, in a treatment room 11, when a doctor or nurse manipulates a call signal generator 11a, the robot 20 waiting receives a call signal through the communication unit 25, moves along the travel detection line 15, and arrives at the treatment room 11 that has sent the call signal. At this time, the storage box 40 is located at a bottom dead center, and the slide 43 is also kept horizontal.

The doctor or nurse puts used treatment tools into the storage box 40 of the robot 20 that has arrived, and then sends the robot 20 to the disinfection room 13. A command may be input to the control unit 23 to send the robot 20 to the disinfection room 13.

After entering the disinfection room 13, the robot 20 approaches the sink 13a as shown in FIG. 8A.

As shown in FIG. 8B, when the robot 20 completely approaches the sink 13a, the elevating actuator 31 is driven to raise the storage box 40. When the height sensor 37 detects the to-be-sensed member 13c as the storage box 40 rises, the storage box 40 is stopped.

Then, the linear motor 35 is operated to move the storage box 40 forwards so that the outlet 41e of the storage box 40 is positioned vertically above the disinfection tank 13b. When the position of the storage box 40 is set, the slide 43 is tilted in the direction indicated by arrow g in FIG. 7A. As the slide 43 tilts forward, the accommodated treatment tool slides down and falls into the disinfection tank 13b. The movement of the treatment tool used in the treatment room 11 to the disinfection tank 13b is completed. When the above process is completed, the storage box is returned to its original position and returned to the wireless charging room 17.

While the present invention has been particularly shown and described with reference to exemplary embodiments thereof, it will be understood by those of ordinary skill in the art that various changes in form and details may be made therein without departing from the spirit and scope of the present invention as defined by the following claims.

DESCRIPTION OF REFERENCE NUMERALS

| | | |
|---|---|---|
| 10: indoor space | 11: treatment room | 11a: call signal generator |
| 13: disinfection room | 13a: sink | 13b: disinfection tank |
| 13c: to-be-sensed member | | |
| 15: travel detection line | | |
| 17: wireless charging room | | |
| 17a: wireless power transmission unit | | |
| 20: robot | 21: main body | 21a: space |
| 23: control unit | 23c: button | 23d: lamp |
| 23e: speaker | 25: communication unit | |
| 27: obstacle sensor | 29: tracking sensor | |
| 31: elevating actuator | 33: elevating structure | 33a: support plate |
| 33b: side plate | 33e: load bearing | 33f: support ball |
| 35: linear motor | 35a: fixing body | 35b: actuation motor |
| 35c: support block | 35e: lead screw | 35f: connecting block |
| 37: height sensor | 40: storage box | 41: casing |
| 41a: connector fixing unit | | |
| 41d: inlet | 41e: outlet | 41f: bearing mounting groove |
| 43: slide | 43a: support pin | 45: opening/closing actuator |
| 45c: connecting pin | 51: wireless power reception unit | |
| 55: battery | 57: wheel | |

The invention claimed is:

1. A robot for transporting patient treatment tools, the robot reciprocating between a treatment room having a call signal generator installed therein and a disinfection room, visiting, in response to a call signal the treatment room where the call signal has been generated, receiving a treatment tool discharged from the treatment room, and transporting the received treatment tool to the disinfection room, the robot comprising:

a main body providing a space open in a front side of the main body and capable of traveling on the ground;

a communication unit installed in the main body and wirelessly connected to the call signal generator;

a control unit located on an upper side of the main body and manipulated by a user;

an elevating structure slidably installed in the space of the main body;

elevating means for elevating the elevating structure;

a storage box supported by the elevating structure, temporarily accommodating treatment tools introduced from the outside, being movable forwards and backwards, and moving forwards and opened to send the treatment tools to the outside; and a storage box driving unit for moving the storage box forwards and backwards, wherein in the disinfection room, a sink having a disinfection tank is installed, and a to-be-sensed member that informs the robot of the height of the disinfection tank is provided on a front surface of an upper end of the sink, the elevating structure comprises: a support plate that maintains a level; load bearings fixed onto an upper surface of the support plate in parallel to each other, extending forwards and backwards, and movably supporting the storage box; and side plates fixed vertically on both sides of the supporting plate, a height sensor for sensing the to-be-sensed member and generating a signal when the support plate is located at the same height as the to-be-sensed member is installed in the elevating structure, and the storage box driving unit is a linear motor that provides a transfer force to the storage box while being mounted on the elevating structure.

2. The robot of claim 1, wherein the storage box comprises:

a casing having an inlet in an upper portion of the storage box and an outlet in a front portion of the storage box and reciprocating by a linear motor while being supported by the load bearings; and an outlet opening/closing unit accommodated in the casing and serving to receive and support treatment tools introduced from the outside through the inlet and to open or block the outlet by moving due to an external force.

3. The robot of claim 2, wherein
the outlet is located eccentrically on a lower portion of a front surface of the casing, and the outlet opening/closing unit comprises:
- a slide being a rectangular plate member, being supported through a support pin within the casing, being rotatable about the support pin, maintaining a height higher than the outlet in a horizontal state, and blocking the outlet while supporting the treatment tool to be discharged; and
- an opening/closing actuator linked to the slide, and keeping the slide horizontal or being inclined toward the outlet so that the treatment tool slides on the slide to pass through the outlet.

* * * * *